United States Patent [19]

Hauptreif et al.

[11] Patent Number: 5,245,081
[45] Date of Patent: Sep. 14, 1993

[54] PREPARATION OF N,N-DISUBSTITUTED M-AMINOPHENOLS

[75] Inventors: Manfred Hauptreif, Ludwigshafen; Helmut Reichelt, Neustadt, both of Fed. Rep. of Germany

[73] Assignee: BASF Aktiengesellschaft, Ludwigshafen, Fed. Rep. of Germany

[21] Appl. No.: 886,843

[22] Filed: May 22, 1992

[30] Foreign Application Priority Data

May 23, 1991 [DE] Fed. Rep. of Germany ....... 4116830

[51] Int. Cl.$^5$ ............................................ C07C 209/18
[52] U.S. Cl. ................................................. 564/403
[58] Field of Search ........................ 564/403, 404, 408

[56] References Cited

U.S. PATENT DOCUMENTS 4,067,903  1/1978  Hoch et al. ................ 260/570.6
5,130,489  7/1992  Dressler .......................... 564/403

FOREIGN PATENT DOCUMENTS 0218350   4/1987  European Pat. Off. .
0402935  12/1990  European Pat. Off. .
2900193   7/1980  Fed. Rep. of Germany .
2385683  10/1978  France .
0053250  10/1978  Japan .
62048653  8/1985  Japan .
62048654  8/1985  Japan .
0061955  12/1985  Japan .

OTHER PUBLICATIONS

Patent Abstracts of Japan, vol. 11, No. 60 (C-405), Oct. 1, 1986, and JP-A-61-221-155, Iwakura Ken, "Separation of Hydroxytriarylamine".
Patent Abstracts of Japan, vol. 16, No. 289 (C-956), Mar. 11, 1992, and JP-A-40-77-460, Nakatsuka Masakatsu, et al., "Production of 3-N-Cyclohexylaminophenol Derivative".

Primary Examiner—Glennon H. Hollrah
Assistant Examiner—Brian Burn
Attorney, Agent, or Firm—Oblon, Spivak, McClelland, Maier & Neustadt

[57] ABSTRACT

The preparation of N,N-disubstituted m-aminophenols from resorcinol, which is reacted, in a first step, with primary amines to form N-monosubstituted m-aminophenols, which are treated in situ, in a second step, with alkylating agents to form N,N-disubstituted m-aminophenols.

9 Claims, No Drawings

PREPARATION OF N,N-DISUBSTITUTED M-AMINOPHENOLS

The present invention relates to a novel process for the preparation of N,N-disubstituted m-aminophenols from resorcinol, which is reacted, in a first step, with primary amines to form N-monosubstituted m-aminophenols, which are treated, in a second step, with alkylating agents to form said N,N-disubstituted m-aminophenols.

DE-A 2,900,193 discloses the reaction of resorcinol with cyclic secondary amines in the presence of phosphorous acid or esters thereof. This produces N,N-disubstituted m-aminophenols containing a heterocyclic radical as substituted amino group.

However, the literature proposes other methods of synthesizing such N,N-disubstituted m-aminophenols in which the substituents on the amino group are, for example, alkyl or cycloalkyl groups.

Thus JP-A 61,955/1987 describes the preparation of m-(N,N-diethylamino)phenol by alkylating m-aminophenol with ethyl chloride. JP-A 48,653/1987 and JP-A 48,654/1987 describe the corresponding reaction for m-(N-ethylamino)phenol as starting material.

In each case, the starting product must be synthesized from resorcinol and ammonia or a primary amine in a separate reaction, as described for example in JP-A 53,250/1980, and then purified before further treatment. Such intermediate purification is usually very costly (cf. EP-A 402,935).

It is thus an object of the present invention to provide a novel process for the preparation of N,N-disubstituted m-aminophenols which produces the target products in a simple manner and can dispense with purification of intermediates.

We have now found that the preparation of an m-aminophenol of formula I

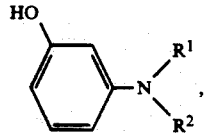  (I)

in which
$R^1$ denotes $C_2$–$C_8$-alkyl or $C_5$–$C_7$-cycloalkyl and
$R^2$ denotes $C_1$–$C_8$-alkyl or $C_5$–$C_7$-cycloalkyl,
is carried out to advantage when, a) in a first step, resorcinol is reacted in the presence of phosphorous acid, an ester of phosphorous acid, or a mixture thereof, with an amine of formula II $$R^1-NH_2 \quad (II),$$

in which $R^1$ has the meaning stated above, at a temperature of from 180° to 250° C. and a pressure of from 3 to 40 bar, after which, b) in a second step, the resulting aminophenol of formula III

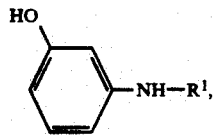  (III)

in which $R^1$ has the meaning stated above, is treated, without intermediate purification, with an alkylating agent of formula IV $$R^2-X \quad (IV),$$

in which $R^2$ has the meaning stated above and X denotes a leaving group, at a temperature of from 60° to 180° C. and a pressure of from 1 to 50 bar in aqueous medium at a pH of from 3 to 7.

All of the alkyl groups occurring in the above formula I may be linear or branched.

Examples of radicals $R^1$ and $R^2$ are ethyl, propyl, isopropyl, butyl, isobutyl, s-butyl, t-butyl, pentyl, isopentyl, neopentyl, t-pentyl, hexyl, 2-methylpentyl, heptyl, 2-methylhexyl, octyl, 2-methylheptyl, 2-ethylhexyl, cyclopentyl, cyclohexyl, and cycloheptyl.

The radical $R^2$ may also be methyl.

In the first step, the resorcinol is preferably reacted with an amine of formula II in which $R^1$ denotes $C_2$–$C_6$-alkyl or cycloalkyl, preferably $C_4$–$C_6$-alkyl and more preferably $C_4$-alkyl.

In the second step, it is preferred to react the aminophenol of formula III with an alkylating agent of formula IV in which $R^2$ denotes $C_1$–$C_4$-alkyl, preferably $C_4$-alkyl.

X in formula IV denotes a leaving group. Suitable leaving groups are, for example, halogen such as chlorine, bromine, and iodine, methosulfate, ethosulfate, benzenesulfonate, and 2- and 4-methylbenzenesulfonates.

Suitable esters of phosphorous acid for use in the first step of the process of the invention are, for example, triphenyl phosphite and $C_1$–$C_8$-trialkyl phosphites such as trimethyl phosphite, triethyl phosphite, tripropyl phosphite, triisopropyl phosphite, tributyl phosphite, triisobutyl phosphite, tri-s-butyl phosphite, tripentyl phosphite, triisopentyl phosphite, trineopentyl phosphite, trihexyl phosphite, triheptyl phosphite, trioctyl phosphite, and tris(2-ethylhexyl) phosphite.

Use is preferably made of phosphorous acid, triphenyl phosphite, a $C_1$–$C_4$-trialkyl phosphite or a mixture of these, but more preferably use is made of phosphorous acid.

The first step of the process of the invention may be carried out continuously or batchwise and advantageously comprises placing resorcinol, the amine of formula II, a diluent if necessary, and phosphorous acid and/or an ester of phosphorous acid, in a pressure vessel and then heating the resulting mixture at autogenous pressure or in the presence of additional inert gas (e.g. nitrogen) to a temperature of from 180° to 250° C., preferably from 190° to 210° C. The pressure in the vessel is usually from 3 to 40 bar and preferably from 10 to 20 bar.

On completion of the reaction, which generally takes from 10 to 20 hours, the reaction mixture is cooled and depressurized. If diluent is present, this may be distilled off, but otherwise the mixture will be directly used for the alkylation reaction in stage 2, that is to say, it will not be subjected to an intermediate purifying operation.

The amount of phosphorous acid, an ester of phosphorous acid, or a mixture of phosphorous acid and ester thereof, usually ranges from 1 to 20% w/w, preferably from 2 to 10% w/w, and is more preferably about 5% w/w, based on the weight of resorcinol used.

The molar ratio of amine II to resorcinol, as required for optimum reaction, is generally from 1:2 to 2:1, preferably from 1:1 to 1.2:1.

Alternatively, the reaction may be carried out using a large excess of amine II, in which case the excess amine II acts as diluent.

Other suitable diluents are inert organic solvents such as toluene and xylene.

We prefer to carry out the first step of the process of the invention substantially in the absence of a diluent.

The second step of the process of the invention may be carried out continuously or batchwise and advantageously comprises placing the reaction mixture resulting from the first step and containing the amine of formula III in a vessel and adding thereto water and the alkylating agent of formula IV.

This mixture is then heated to a temperature of from 60° to 180° C., preferably from 60° to 130° C., and an alkali metal hydroxide solution is added at such a rate that the pH of the reaction mixture is held between 3 and 7, preferably between 4 and 5. This alkylation is usually carried out under a pressure of from 1 to 50 bar. The autogenous pressure which results within this range depends on the boiling point of the alkylating agent IV.

On completion of the reaction, which generally takes from 4 to 9 hours, the reaction mixture is cooled and, where necessary, depressurized.

The target product I can be isolated from the reaction mixture in conventional manner, for example by separating the organic phase. The organic phase can then be washed and subjected to distillation.

The amount of alkylating agent IV is usually from 1 to 2 moles and preferably from 1 to 1.2 moles, for each mole of amine II.

The aqueous alkali metal hydroxide solution used is for example an aqueous sodium or potassium hydroxide solution having a concentration of sodium or potassium hydroxide of from 5 to 50% w/w, preferably 20 to 30% w/w. For each mole of alkylating agent IV there will normally be used from 0.9 to 11 moles of alkali metal hydroxide.

The amount of water added to the amine III during alkylation is usually from 2 to 5 times the weight of resorcinol used.

If desired, the alkylation reaction may be carried out under a blanket of protective gas, e.g. nitrogen, and in the presence of small amounts of sodium or potassium iodide and/or a surfactant such as a benzyltrialkylammonium compound.

The novel process makes it possible to synthesize N,N-disubstituted m-aminophenols in good yields and in a high state of purity. The process is simple to carry out on an industrial scale, and the isolation and purification of the N-monosubstituted m-aminophenol formed as intermediate can be omitted. Another advantage of the novel process is the fact that it can be carried out in a single vessel.

The N,N-disubstituted m-aminophenols of formula I are important intermediates for the synthesis of fluorans, which are useful as color formers (cf. for example U.S. Pat. No. 3,873,573).

The invention is further illustrated by the following Examples.

EXAMPLE 1 a) 660 g of resorcinol, 483 g of n-butylamine, and 33 g of phosphorous acid were heated in an autoclave under nitrogen for 8 hours to a temperature of 200° C., during which time the pressure in the autoclave rose to 13 bar. The mixture was then cooled and depressurized.

b) To the reaction mixture (1,200 g) obtained in step a) there were added, under a blanket of nitrogen, 1.8 l of water, 863 g of bromobutane, 3.5 g of potassium iodide, and 3 g of a surfactant based on a benzyltrialkylammonium compound, and the whole was heated to 60° C. At this temperature, 770 g of 25% w/w caustic soda solution were added dropwise during the course of 12 hours such that the pH of the reaction mixture remained constant at a value of 5. The mixture was then heated to 80° C., and at this temperature a further 125 g of 25% w/w caustic soda solution were added dropwise over 8 hours. Here again, the pH of the reaction mixture was kept at 5. The mixture was then cooled, and 160 ml of water were added. The aqueous phase was separated off and the organic phase (950 g) was washed with water. After the removal of residues, the organic phase was subjected to distillation under reduced pressure (10 mbar). The yield of m-dibutylaminophenol was 850 g, and its purity, as determined by HPLC, was 97%.

EXAMPLE 2 a) 14,52 kg of resorcinol, 10.74 kg of n-butylamine, and 0.734 kg of phosphorous acid were heated, in an autoclave under nitrogen to a temperature of 200° C. over a period of 6 hours, during which time the pressure rose to 12 bar. The autoclave was then cooled and depressurized.

b) To the reaction mixture (26 kg) obtained in step a) there were added, under a blanket of nitrogen, 40 l of water, 14.52 kg of chlorobutane, and 0.33 kg of a surfactant based on a benzyltrialkylammonium compound, and the whole was heated to 120° C. At this temperature, 15 l of 25% w/w caustic soda solution were added dropwise during the course of 20 hours such that the pH of the reaction mixture remained constant at a value of 5. The mixture was then cooled, and the aqueous phase was separated off and the organic phase washed with 25 l of water. After the removal of residues, the organic phase was subjected to distillation under reduced pressure (10 mbar).

The yield of m-dibutylaminophenol was 19.01 kg, and its purity, as determined by GC, was 98.5%.

EXAMPLE 3 a) 11 kg of resorcinol, 8.05 kg of n-butylamine, and 0.433 kg of phosphorous acid were heated, in an autoclave under nitrogen, to a temperature of 200° C. over a period of 6 hours, during which time the pressure rose to 12 bar. The autoclave was then cooled and depressurized.

b) To the reaction mixture (19.5 kg) obtained in step a) there were added, under a blanket of nitrogen, 45 l of water, 14.52 kg of chlorobutane, and 0.33 kg of a surfactant based on a benzyltrialkylammonium compound, and the whole was heated to 120° C. 10.4 l of 25% w/w caustic soda solution were then added dropwise during the course of 6 hours such that the pH of the reaction mixture remained constant at a value of 5. During this period, the temperature was steadily raised from 120° C. to 160° C. The mixture was then worked up in a manner similar to that described in Example 2b.

The yield of m-dibutylaminophenol was 15.5 kg, and its purity, as determined by GC, was 98.6%.

EXAMPLE 4 a) 11 kg of resorcinol, 9.2 kg of isopentylamine, and 0.55 kg of phosphorous acid were heated, under nitrogen in an autoclave, to a temperature of 200° C. over a period of 6 hours. The autoclave was then cooled and depressurized.

b) To the reaction mixture (20 kg) obtained in step a) there were added, under a blanket of nitrogen, 40 l of water, 6.5 kg of chloroethane, and 0.33 kg of a surfactant based on a benzyltrialkylammonium compound, and the whole was heated to 120° C. At this temperature, 15 l of 25% w/w caustic soda solution were added dropwise during the course of 20 hours such that the pH of the reaction mixture remained constant at a value of 5. The mixture was then cooled, and the aqueous phase was separated off and the organic phase washed with 25 l of water. After the removal of residues, the organic phase was subjected to distillation under reduced pressure (10 mbar).

The yield of N-isopentyl-N-ethyl-m-aminophenol was 13.2 kg, and its purity, as determined by GC, was 98%.

The compounds listed in the Table below and having the following formula

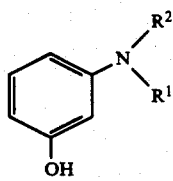

were synthesized in a manner similar to that described in Example 3.

| Example No. | $R^1$ | $R^2$ |
|---|---|---|
| 5 | methyl | cyclohexyl |
| 6 | ethyl | ethyl |
| 7 | n-propyl | n-propyl |
| 8 | n-pentyl | n-pentyl |

We claim:

1. A process for the preparation of an m-aminophenol of formula I

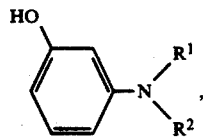

in which
$R^1$ denotes $C_2$–$C_8$-alkyl or $C_5$–$C_7$-cycloalkyl and
$R^2$ denotes $C_1$–$C_8$-alkyl or $C_5$–$C_7$-cycloalkyl, wherein,
a) in a first step, resorcinol is reacted in the presence of phosphorous acid, an ester of phosphorous acid, or a mixture thereof, with an amine of formula II $$R^1-NH_2 \qquad (II),$$

in which $R^1$ has the meaning stated above, at a temperature of from 180° to 250° C. and a pressure of from 3 to 40 bar, after which,
b) in a second step, the resulting aminophenol of formula III

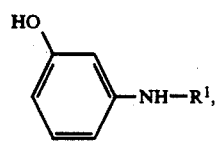

in which $R^1$ has the meaning stated above, is treated, without intermediate purification, with an alkylating agent of formula IV $$R^2-X \qquad (IV),$$

in which $R^2$ has the meaning stated above and X denotes a leaving group, at a temperature of from 60° to 180° C. and a pressure of from 1 to 50 bar in aqueous medium at a pH of from 3 to 7 wherein said process is conducted in a single vessel.

2. A process as claimed in claim 1, wherein resorcinol is reacted with an amine of formula II in which $R^1$ denotes $C_2$–$C_6$-alkyl or cyclohexyl.

3. A process as claimed in claim 1, wherein the alkylation is carried out using an alkylating agent of formula IV in which $R^2$ denotes $C_1$–$C_4$-alkyl.

4. The process of claim 1, wherein said first step is conducted at a temperature of from 190° to 210° C.

5. The process of claim 1, wherein said first step is conducted at a pressure of from 10 to 20 bar.

6. The process of claim 1, wherein in said first step, resorcinol is reacted with 1-20% wt./wt. of phosphorous acid, an ester of phosphorous acid or a mixture thereof.

7. The process of claim 1, wherein the ratio of said amine of formula (II) to resorcinol is 1:2 to 2:1.

8. The process of claim 1, wherein the pH of said second step is regulated with an alkali metal hydroxide.

9. The process of claim 1, wherein said second step is conducted at a pH of from 4 to 5.

* * * * *